United States Patent
Orbay

(10) Patent No.: US 6,533,788 B1
(45) Date of Patent: Mar. 18, 2003

(54) LOCKING DEVICE FOR INTRAMEDULLARY PIN FIXATION

(75) Inventor: Jorge L. Orbay, Miami, FL (US)

(73) Assignee: Hand Innovations, Inc., Miami, FL (US)

(*) Notice: Subject to any disclaimer, the term of this patent is extended or adjusted under 35 U.S.C. 154(b) by 0 days.

(21) Appl. No.: 10/016,457

(22) Filed: Nov. 1, 2001

(51) Int. Cl.$^7$ ................................................ A61B 17/58
(52) U.S. Cl. .............................. 606/62; 606/63; 606/64
(58) Field of Search ............................ 606/62, 63, 64, 606/65, 66, 67, 68, 96, 98, 104, 77

(56) References Cited

U.S. PATENT DOCUMENTS

| | | | |
|---|---|---|---|
| 3,892,232 A | 7/1975 | Neufeld ........................ 128/92 |
| 4,169,470 A | 10/1979 | Ender et al. .................. 128/92 |
| 4,381,770 A * | 5/1983 | Neufeld ........................ 606/67 |
| 4,522,200 A | 6/1985 | Stednitz ........................ 128/92 |
| 4,790,304 A | 12/1988 | Rosenberg .................... 128/92 |
| 4,969,887 A * | 11/1990 | Sodhi ............................ 606/67 |
| 5,207,753 A | 5/1993 | Badrinath ..................... 606/96 |
| 5,257,996 A | 11/1993 | McGuire ...................... 606/104 |
| 5,281,225 A | 1/1994 | Vicenzi ......................... 606/62 |
| 5,330,468 A * | 7/1994 | Burkhart ....................... 606/96 |
| 5,391,171 A | 2/1995 | Schmieding ................. 606/104 |
| 5,400,805 A | 3/1995 | Warren ......................... 128/898 |
| 5,667,510 A | 9/1997 | Combs .......................... 606/86 |
| 5,893,850 A | 4/1999 | Cachia .......................... 606/72 |
| 6,053,918 A * | 4/2000 | Spievack ...................... 606/64 |
| 6,074,392 A | 6/2000 | Durham ........................ 606/67 |
| 6,200,321 B1 | 3/2001 | Orbay et al. .................. 606/96 |
| 6,273,892 B1 | 8/2001 | Orbay et al. .................. 606/96 |

FOREIGN PATENT DOCUMENTS

DE     3924610 A1     3/1990

* cited by examiner

Primary Examiner—Pedro Philogene
(74) Attorney, Agent, or Firm—David P. Gordon; David S. Jacobson; Thomas A. Gallagher

(57) ABSTRACT

A locking device includes a locking sleeve and a handle. The locking sleeve defines a pin channel and a plurality of resilient locking catches. The distal end of the sleeve includes a tip having a cutting edge and a pin guide adapted to be located about a portion of the diameter of a fixation pin. The locking sleeve is used to stabilize the location and orientation of a fixation pin implanted in a bone.

22 Claims, 4 Drawing Sheets

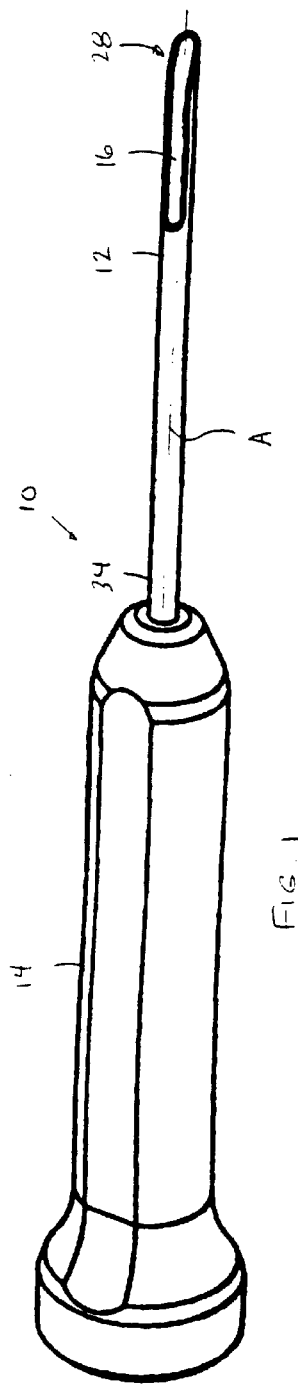
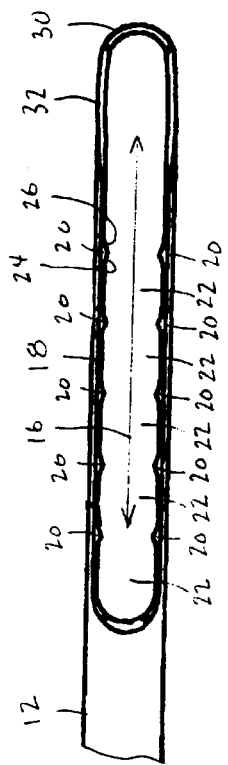
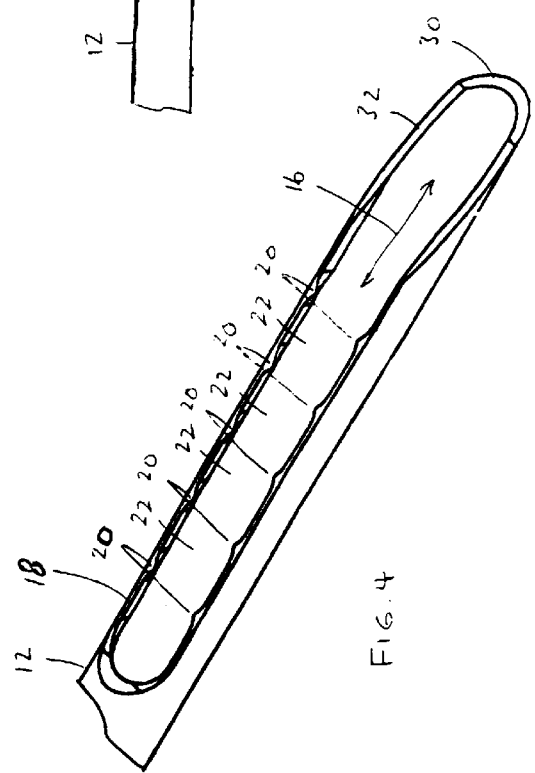

LOCKING DEVICE FOR INTRAMEDULLARY PIN FIXATION

BACKGROUND OF THE INVENTION

1. Field of the Invention

This invention relates broadly to a system for bone fracture fixation. More particularly, this invention relates to a system and method for fixation pin stabilization within a fractured bone.

2. State of the Art

Metacarpal fractures are very common. Immobilization of the metacarpal bone on either side of the fracture is imperative for proper healing. However, the location of the fracture presents several difficulties to ideal immobilization.

The most frequently used treatments for immobilizing the fracture are splinting and casting. However, due to the location of the metacarpal bones, these treatments fail to maintain proper fracture reduction in the metacarpal bones. Strong fixation is possible with techniques using plates, fixation screws, and fixation pins attached to the affected bones through operative treatment. While these types of fracture reduction devices are commonly used in larger bone fractures, e.g., ulnar, tibial, or femoral fractures, such operative treatment generally implies a formidable incision and exposure of the fracture site. Therefore, these techniques are often judged to be too invasive for the relatively small and fragile metacarpal bones.

An alternative less invasive technique has been used in which a small incision is made in the skin proximal the metacarpal bone, a boring tool is inserted through the incision and is used to drill a small hole into the metacarpal bone, the boring tool is removed, and then the physician feeds the pin through the incision and into the small unseen bore in the bone. However, feeding the pin through the skin is often a blind operation with no manner provided for indicating to the physician the relative location of the pin and the small hole bored in the bone. As such, the technique is objectionable to both physician and patient as blind feeding can result in exacerbating damage to the surrounding tissue. In addition, the implanted pin fails to provide torsional fixation for fractures which need to be rotationally immobilized. Similar problems exist with respect to metatarsal and phalangeal fractures.

Co-owned U.S. Pat. Nos. 6,200,321 and 6,273,892, which are hereby incorporated by reference herein in their entireties but which are not admitted as prior art hereto, disclose systems for inserting pins into a metacarpal, metatarsal, phalangeal, and other small bones without the drawbacks associated with blind pin insertion. In addition, U.S. Pat. No. 6,273,892 discloses a collet which can be used to provide torsional fixation of an implanted pin. However, the collet is small and difficult to handle, requires a relatively large bone mass permitting an end of the collet to be tapped into the bone, and is relatively time consuming to implant. As such, it would be desirable to have a device which provides stabilization for an implanted pin, but which overcomes the stated drawbacks of the prior device.

SUMMARY OF THE INVENTION

It is therefore an object of the invention to provide a device which locks a fixation pin in the metacarpal, metatarsal, or phalangeal bones, or bones of similar structure.

It is another object of the invention to provide a device which provides torsional and longitudinal stability to the fixation pin and thereby to the bone through which the fixation pin extends.

It is also an object of the invention to provide a device which can be implanted relatively easily and quickly.

It is a further object of the invention to provide a fracture fixation system which provides a fixation system which is relatively easy to manipulate.

In accord with these objects, which will be discussed in detail below, a locking device including a locking sleeve and a handle is provided. The locking sleeve is preferably a metal tubular cylindrical member having a longitudinal axis and defining a channel parallel to the axis. The cylindrical member has a diameter sized to receive a first portion of a fixation pin, and preferably a plurality of resilient locking catches adapted to hold a second portion of the fixation pin angled relative to the first portion. The distal end of the sleeve includes a tip which is preferably provided with a distalmost cutting edge and an adjacent pin guide adapted to be located about a portion of the diameter of a fixation pin. The handle is coupled to the proximal end of the sleeve to facilitate manipulation of the sleeve.

The locking sleeve is used to stabilize the location and orientation of a fixation pin implanted in a bone. Such an implanted pin has a central portion which extends across the fracture, a distal end which extends preferably to the distal end of the medullary canal of the bone, and a proximal portion which protrudes from the proximal end of the bone and above the skin surface. The proximal portion is angled relative to the central portion along a bent portion therebetween.

According to the invention, the distal end of the locking sleeve is fed over the proximal end of the pin and then manipulated with the handle such that the guide portion of the distal end of the sleeve is placed against the pin with the cutting edge against the skin. The cutting edge is then pushed to pierce the skin, pass through the tissue in the hand, and enter the bone surrounding the existing entry hole used for pin insertion. As the locking sleeve is pushed into the tissue and bone, the resilient catches of the sleeve are pushed over the bent portion of the pin (generally at the intersection of the central and proximal portions), with the bent portion effectively snap fitting between longitudinally adjacent catches as the sleeve is moved thereover. The sleeve is pushed into the bone until sufficiently seated for stabilized support, e.g., with the cutting edge extending from one side of the medullary canal, across the canal, and into the bone on the opposite side until it meets the cortex. The sleeve and pin are then preferably cut below the skin. Thus, the sleeve implanted in the bone stabilizes the pin during healing of the fracture.

If more than one pin is used to stabilize a fracture, a locking sleeve may be used for each pin.

Additional objects and advantages of the invention will become apparent to those skilled in the art upon reference to the detailed description taken in conjunction with the provided figures.

BRIEF DESCRIPTION OF THE DRAWINGS

FIG. 1 is a locking device for locking a pin in a bone according to the invention;

FIG. 2 is a broken top view of the distal end of the locking device of FIG. 1;

FIG. 3 is a side elevation view of the distal end of the locking device of FIG. 1;

FIG. 4 is a broken perspective view of the distal end of the locking device of FIG. 1;

DETAILED DESCRIPTION OF THE PREFERRED EMBODIMENTS

Figure 5:
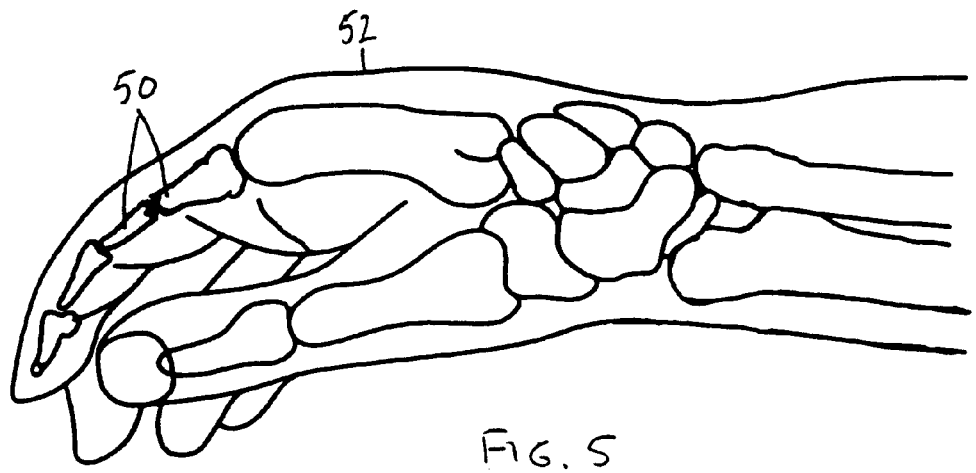
FIG. 5 is a transparent schematic view of a human hand having a fractured metacarpal bone.

Turning now to FIGS. 1 through 4, a locking device 10 according to the invention is shown. The locking device 10 includes a locking sleeve 12 and a handle 14. The locking sleeve 12 is preferably a metal, e.g., titanium alloy or stainless steel, tubular member having a longitudinal axis A and defining a channel 16 parallel to the axis. The channel 16 is sized to receive a portion of a fixation pin, as described in detail below. The channel 16 defines an open surface 18 to the tubular member which includes a plurality of spaced-apart pairs of catches 20. The catches 20 define keyholes 22 which are each adapted to receive another portion of a fixation pin, as also described below. Each of the catches 20 preferably has ramped rear and forward sides 24, 26. As such, when an object, such as a portion of a fixation pin, is sufficiently forced against the ramped sides of the catches, the opening 18 of the channel 16 tends to widen. However, the sleeve 12 is sufficiently resilient that once the force is removed, the open surface 18 returns to its previous dimension. The space between each catch 20 in a pair is preferably smaller than the diameter of the fixation pin for which the sleeve 12 is designed.

The distal end 28 of the sleeve 12 includes a distalmost cutting edge 30 and an adjacent pin guide 32 which is sloped from the cutting edge toward the catches.

The proximal end 34 of the sleeve 12 is preferably glued into a bore (not shown) in the handle 14 with cyanoacrylate. This secure coupling facilitates manipulation of the sleeve. The handle is preferably molded from plastic, e.g., ABS, nylon, polycarbonate, or polyethylene, but may be machined from a Delrin™ rod or a similar material.

According to one preferred, but only exemplar, embodiment of the invention, the length of the sleeve 12 extending from the handle 14 is approximately two inches. The tubular portion of the sleeve 12 has an inner diameter of approximately 0.062 inches, and the length from the rear of the open surface 18 to the cutting edge 30 is approximately 0.6 inches. The catches 20 are longitudinally spaced along 0.38 inches of the distal portion of the sleeve 12, and the pin guide 32 and cutting edge 30 together extend along 0.22 inches of the distal portion of the sleeve 12. The catches 20 are longitudinally spaced apart by approximately 0.075 inches, with the space between each catch in a pair being approximately 0.055 inches. The keyhole spaces 22 defined between two pairs of catches is approximately 0.043 inches. The pin guide 32 is angled downward from the open surface 18 toward the cutting edge 30 by approximately 15°, and the cutting edge 30 is angled downward from the pin guide 32 by approximately 25°.

Figure 6:
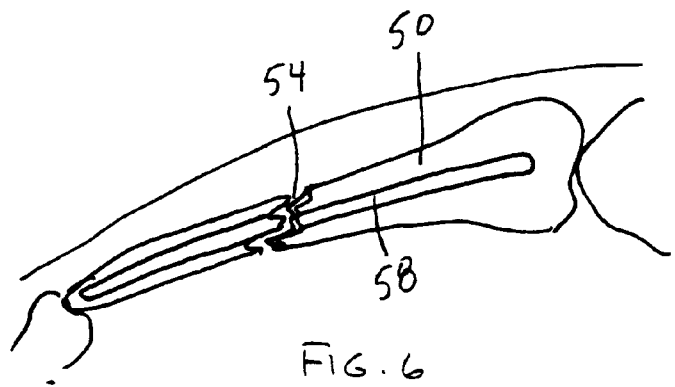
FIG. 6 is an enlarged view of the fractured metacarpal in FIG. 5.
Figure 7:
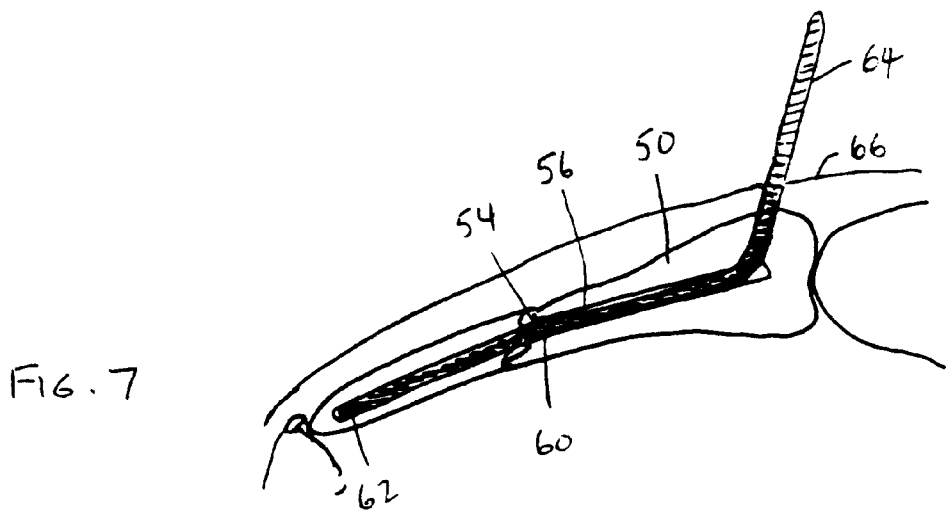
FIG. 7 is a schematic illustration of the insertion of a fixation pin into the fractured metacarpal bone.

In use, the locking sleeve 12 of the device 10 is used to stabilize the location and orientation of a fixation pin implanted in a bone. Referring to FIGS. 5 and 6, when a small elongate bone, e.g., the metacarpal bone 50 of the hand 52, is broken, it is desirable to stabilize the fracture 54 with a pin. Referring to FIGS. 6 and 7, according to any method known in the art, but preferably according to the method disclosed in co-owned U.S. Pat. Nos. 6,200,321 and 6,273,892, already incorporated herein, a fixation pin 56 is inserted in the medullary canal 58 of the metacarpal bone 50. The implanted pin 56 has a central portion 60 which extends across the fracture 54, a distal end 62 which preferably extends to the distal end of the medullary canal of the bone, and a proximal portion 64 which extends from the bone 50 and protrudes from the skin surface 66. The proximal portion 64 is preferably bent at a 90° to 110° angle relative to the central portion 60 at, along, or near a location 78 (FIG. 8) such that a bent portion 79 is defined between the proximal and central portions.

Figure 8:
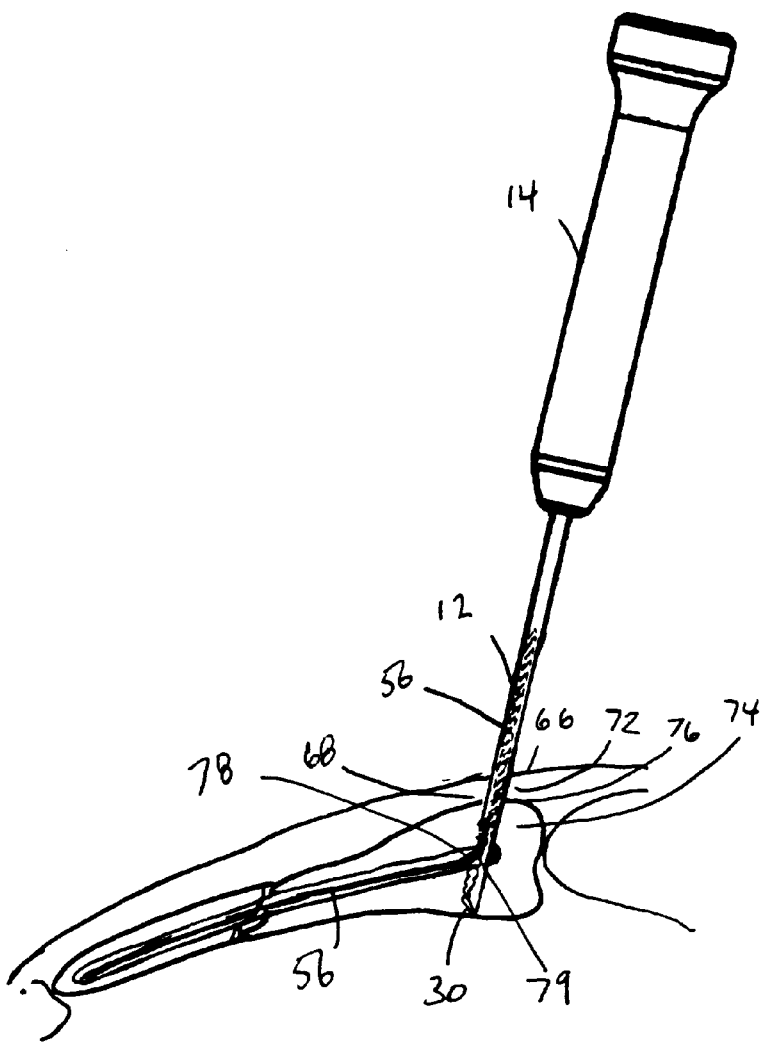
FIG. 8 illustrates insertion of the locking device into the metacarpal bone.

Turning now to FIG. 8, a locking sleeve 12 sized relative to the pin so that the pin will fit in the sleeve (i.e., the inner diameter of the sleeve is larger than the outer diameter of the pin) then placed over the proximal end of the pin and then manipulated with the handle 14 such that the guide portion 32 at the distal end 28 of the sleeve 12 is placed against the pin and the skin of the patient. The cutting edge 30 of the sleeve 12 is then pushed to pierce the skin 66, pass through the tissue 72 in the hand, and enter the bone 74 surrounding the entry hole 76 created during pin implantation.

Figure 9:
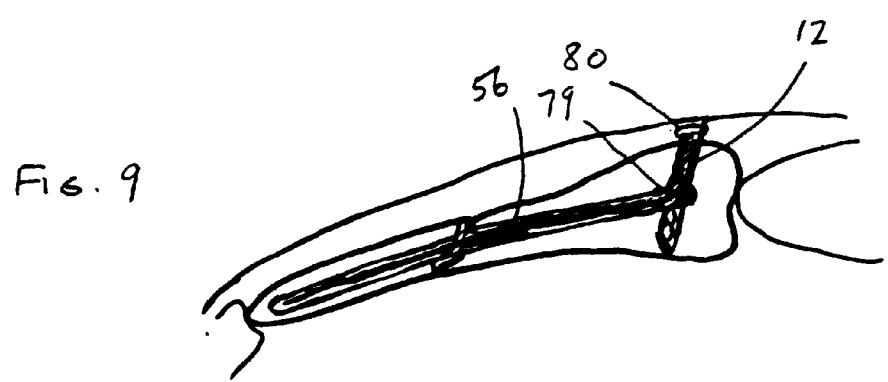
FIG. 9 illustrates the implanted locking device securing the fixation pin in the metacarpal bone.
Figure 12:
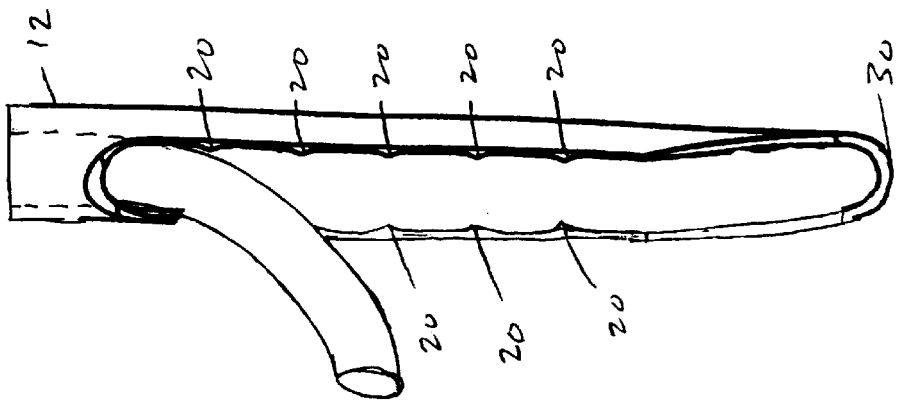
FIG. 12 is a perspective view of the locking device holding the fixation pin.
Figure 11:
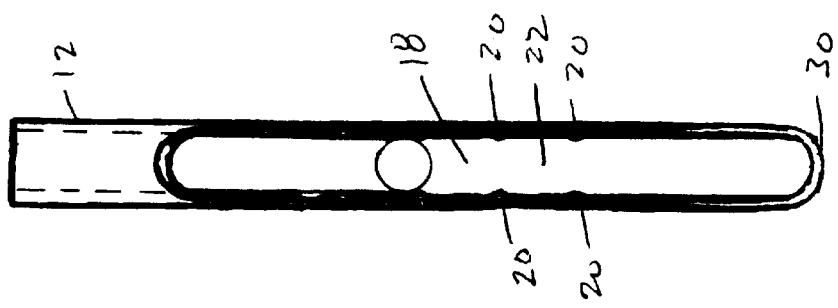
FIG. 11 is a front view of the locking device holding the fixation pin.
Figure 10:
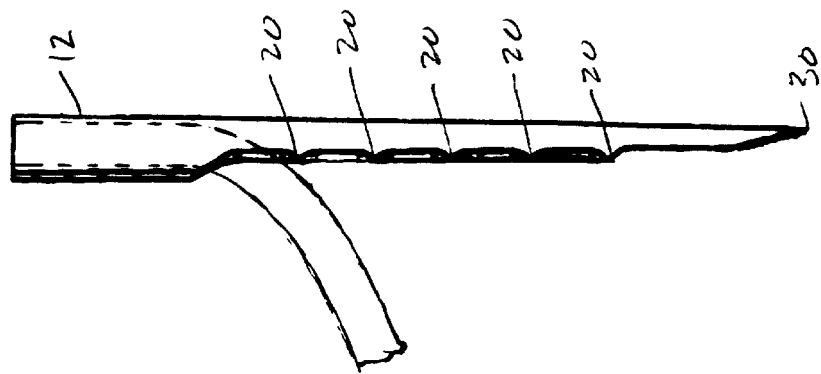
FIG. 10 is a side.elevation view of the locking device holding the fixation pin.

Referring to FIGS. 8 through 12, as the locking sleeve 12 is pushed into the tissue and bone, the resilient catches 20 (FIGS. 2 and 4) are pushed over the location 78 of the bent portion 79, with the location 78 effectively snap fitting into the keyholes 22 as the sleeve 12 is moved thereover. When the sleeve 12 is sufficiently seated in the bone 74 for stabilized support (preferably with the cutting edge 30 extending from one side of the medullary canal, across the canal, and to the cortex on the other side, as shown in FIGS. 8 and 9), the sleeve and pin are together cut, e.g., with a wire cutter or snips, just below the skin, as shown in FIG. 9, and a bandage is preferably provided over the puncture hole to aid in healing.

With the sleeve implanted in the bone as described, the pin 56 is stably held and prevented from both longitudinal and rotational movement. Thus, the sleeve 12 stabilizes the pin 56 during healing of the fracture.

If more than one fixation pin is used to stabilize a fracture, it is appreciated that a locking sleeve may be used for each such fixation pin.

Moreover, if it is necessary to stabilize a fracture of the third or fourth metacarpal bone, it is recognized that the extensor tendons are located at or near the locations at which the sleeve would be implanted. In order to prevent or minimize any irritation which would otherwise occur should the extensor tendon abrade against the cut ends of the sleeve and pin, it is preferably to place a small cap 80 (FIG. 9) over the cut ends to shield the extensor tendons from the cut ends. The cap 80 can be made of metal or plastic, but should provide a low friction interface between the tendons and the cap.

There have been described and illustrated herein an embodiment of a locking sleeve device and method for using the same. While particular embodiments of the invention have been described, it is not intended that the invention be limited thereto, as it is intended that the invention be as broad in scope as the art will allow and that the specification be read likewise. Thus, while the locking sleeve device has been particularly disclosed for use in the fixation of a pin extending through a fractured metacarpal bones, it will be appreciated that the device may similarly be used to fixate bones of similar or smaller size and for which similar problems exist with respect to fracture fixation, e.g., metatarsal bones in the foot and the phalanges of the fingers and toes. In addition, pediatric arm bones, e.g., ulna and radial bones, can be similarly treated. Therefore, the teaching here is for the use of the locking device of the invention with the above mentioned and like bones. Also, while particular materials have been disclosed with respect to the various components of the system of the invention, it will be appreciated that other suitable materials may be used as well. Furthermore, while a plurality of keyholes areas are preferably defined by the sleeve, it will be appreciated that fewer (even one) or more keyholes may be provided. Also, catch elements having a different shape may also be used. Moreover, the catches may be beveled to better accommodate and stably hold pins having bends over a wide range of angles. Furthermore, a handle is not required, but rather preferred to facilitate manipulation of the sleeve. It will therefore be appreciated by those skilled in the art that yet other modifications could be made to the provided invention without deviating from its spirit and scope as claimed.

What is claimed is:

1. A device for stabilizing a fixation pin implanted in a fractured bone, the fixation pin having a first portion, a second portion, and a bent portion between the first and second portions, said device comprising:
    a sleeve having a tubular proximal portion and a distal portion including a channel with an open surface provided with a plurality of resilient catches,
    said proximal portion sized to receive the first portion of said pin.
2. A device according to claim 1, wherein:
    said catches are adapted to at least partially engage the bent portion of the fixation pin.
3. A device according to claim 1, wherein:
    said distal portion includes a distalmost cutting edge.
4. A device according to claim 2, wherein:
    said distal portion includes a ramped portion between said cutting edge and said catches.
5. A device according to claim 1, wherein:
    a plurality of pairs of said catches are longitudinally arranged along said open surface of said channel.
6. A device according to claim 1, wherein:
    a plurality of said catches includes a ramped portion.
7. A device according to claim 1, further comprising:
    a handle coupled to said proximal end of said sleeve.
8. A device according to claim 1, wherein:
    said tubular proximal portion has an inner diameter of approximately 0.0625 inches.
9. A locking device for stabilizing a fixation pin having a first portion, a second portion and a bent portion therebetween, comprising:
    a) first means for receiving the first portion of the fixation pin;
    b) second means for lockably holding the bent portion of the fixation pin; and
    c) third means for cutting bone,
        said first, second and third means having a unitary construct.
10. A locking device according to claim 9, wherein:
    the bent portion defines a 90° to 110° angle between the first and second portions.
11. A locking device according to claim 9, wherein:
    said second means lockably holds the second portion of the fixation pin in one of a plurality of positions relative to said third means.
12. A locking device according to claim 9, wherein:
    said second means substantially prevents both longitudinal and rotational movement of said pin.
13. A locking device according to claim 9, wherein:
    said unitary construct is single tubular element.
14. An assembly of a locking device and a fixation pin, comprising:
    a) a locking device including a proximal tubular portion and a distal portion including a channel with an open surface, said open surface provided with at least one lock portion; and
    b) a fixation pin having a bent portion defining first and second portions angled relative to each other,
        wherein said first portion of said pin at least partially extends within said tubular portion, and said bent portion extends within at least one of said at least one lock portion such that longitudinal and rotational movement of said fixation pin relative to said sleeve is substantially prevented.
15. An assembly according to claim 14, wherein:
    each of said at least one lock portion includes a plurality of catches.
16. An assembly according to claim 14, wherein:
    said distal portion includes a distalmost cutting edge.
17. An assembly according to claim 16, wherein:
    said distal portion includes a guide portion between said cutting edge and said catches.
18. An assembly according to claim 14, further comprising:
    c) a cap adapted to positioned over a cut end of said locking device.
19. A method of stabilizing a fixation pin extending through the skin and into a bone, said method comprising:
    a) inserting a fixation pin into a fractured bone, the pin including a first portion extending upward through the skin and a second portion extending longitudinally through the bone, and a bent portion therebetween;
    b) providing a locking sleeve having a tubular proximal portion and a distal portion including a channel with an open surface, said open surface provided with at least one lock portion;
    c) manipulating the locking sleeve around the first portion of the pin; and
    d) pushing the locking sleeve into the bone at least until the at least one lock portion locks about the second portion of the pin.
20. A method according to claim 19, wherein:
    said locking sleeve includes a distal cutting edge, and said pushing includes pushing the locking sleeve into the bone until the cutting edge moves across a medullary canal of the bone and contacts a cortex of the bone.
21. A method according to claim 19, further comprising:
    e) cutting the locking sleeve to provide a cut end of the locking sleeve below the skin.
22. A method according to claim 21, further comprising:
    f) positioning a cap over the cut end of the locking sleeve.

* * * * *

UNITED STATES PATENT AND TRADEMARK OFFICE
Certificate

Patent No. 6,533,788 B1                          Patented: March 18, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jorge L. Orbay, Miami, FL (US); and Javier Castañeda, Miami, FL (US).

Signed and Sealed this First Day of August 2006.

CORRINE M. MCDERMOTT
*Supervisory Patent Examiner*
Art Unit 3738

UNITED STATES PATENT AND TRADEMARK OFFICE
CERTIFICATE OF CORRECTION

PATENT NO. : 6,533,788 B1 Page 1 of 1
APPLICATION NO. : 10/016457
DATED : March 18, 2003
INVENTOR(S) : Jorge L. Orbay et al.

It is certified that error appears in the above-identified patent and that said Letters Patent is hereby corrected as shown below:

In field (75) of the title page, add "Javier E. Castañeda, Miami, FL (US)"

Signed and Sealed this

Fifth Day of September, 2006

JON W. DUDAS
*Director of the United States Patent and Trademark Office*